(12) United States Patent
Toth et al.

(10) Patent No.: US 6,256,364 B1
(45) Date of Patent: Jul. 3, 2001

(54) METHODS AND APPARATUS FOR CORRECTING FOR X-RAY BEAM MOVEMENT

(75) Inventors: Thomas L. Toth, Brookfield; Roy A. Nilsen, Menomonee Falls, both of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/199,170

(22) Filed: Nov. 24, 1998

(51) Int. Cl.[7] .................................................. G01N 23/00
(52) U.S. Cl. .................................................. 378/4; 378/19
(58) Field of Search ........................................... 378/4–20

(56) References Cited

U.S. PATENT DOCUMENTS

| 4,991,189 | * | 2/1991 | Boomgarden et al. ................. 378/4 |
| 5,200,985 | | 4/1993 | Miller . |
| 5,241,577 | | 8/1993 | Burke et al. . |
| 5,268,955 | | 12/1993 | Burke et al. . |
| 5,274,690 | | 12/1993 | Burke et al. . |
| 5,291,538 | | 3/1994 | Burke et al. . |
| 5,305,363 | | 4/1994 | Burke et al. . |
| 5,485,493 | | 1/1996 | Heuscher et al. . |
| 5,550,886 | * | 8/1996 | Dobbs et al. .......................... 378/19 |
| 5,579,359 | | 11/1996 | Toth . |
| 5,592,523 | | 1/1997 | Tuy et al. . |
| 5,644,614 | | 7/1997 | Toth et al. . |
| 5,761,257 | | 6/1998 | Toth et al. . |

* cited by examiner

*Primary Examiner*—Craig E. Church
(74) *Attorney, Agent, or Firm*—Armstrong Teasdale LLP; Christian G. Cabou (57) ABSTRACT

The present invention, in one form, is a system which, in one embodiment, corrects for position errors of an x-ray beam caused by dynamic movement and thermal drift of the imaging system. More specifically, signals from a detector array are utilized to determine a dynamic movement error to correct for errors caused by the rotation of a gantry and a thermal drift error to correct for imaging system x-ray beam movement errors. In one embodiment, a pre-patient collimator is utilized to alter the z-axis position of the x-ray beam as determined by the dynamic movement and the temperature error profiles.

36 Claims, 4 Drawing Sheets

METHODS AND APPARATUS FOR CORRECTING FOR X-RAY BEAM MOVEMENT

BACKGROUND OF THE INVENTION

This invention relates generally to computed tomography (CT) imaging and more particularly, to correction of z-axis x-ray beam movement in an imaging system.

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

At least one known CT system uses a real-time z-axis beam sensing detector to measure the position of the x-ray beam for each view. From the measured position, an error signal representative of the difference between the measured and desired position is determined. Using the error signal, the position of a collimator may be adjusted to reduce the z-axis error between the measured and desired positions. However, the measured position signal at each view contains noise which may have a standard deviation approaching the z-axis error. Although the noise may be filtered, the filtering causes a phase lag and a position error in following the dynamic movement during the scan. As a result, a compromise must be made between loop response time and beam position measurement noise resulting in significant tracking errors.

Accordingly, it would be desirable to provide a system to facilitate correction of z-axis x-ray beam movement. It would also be desirable to provide such a system which improves image quality without increasing patient dosage.

BRIEF SUMMARY OF THE INVENTION

These and other objects may be attained by a system which, in one embodiment, corrects for position errors, or movements, of an x-ray beam caused by dynamic movement and thermal drift of an imaging system. More specifically and in one embodiment, signals from a detector array are utilized to determine a dynamic movement error and a thermal drift error. Utilizing the dynamic movement error and the thermal drift error, the position of the x-ray beam is corrected for the position errors.

Specifically, the dynamic movement error profile is determined by measuring the position error caused by the rotation of the components within a gantry of the imaging system. Particularly, as a result of the dynamic movement error being consistent from rotation to rotation of the gantry, the determined dynamic movement error for an initial rotation of the gantry may be utilized to correct for dynamic movement errors in subsequent rotations of the gantry. In one embodiment, the dynamic movement error is determined by generating a difference between a measured, or actual, position of the x-ray beam and a desired position of the x-ray beam. By characterizing the difference for a plurality of locations of the gantry, the dynamic movement error is determined.

In addition to the dynamic movement error, the position of the x-ray beam is altered by the thermal drift of the imaging system. In one embodiment, the thermal drift error includes an actual thermal drift from a previous rotation of the gantry and a predicted thermal drift. The predicted thermal drift is determined by generating a difference between a measured x-ray beam position and a desired x-ray beam position for the operating range of an x-ray source as a function of time. Prior to starting a scan, the thermal drift error is utilized to adjust the position of the x-ray beam to correct for the thermal drift of the system.

In one embodiment, the dynamic movement error and the thermal drift error are combined to alter the position of a pre-patient collimator to correct for the dynamic movement and thermal drift errors of the imaging system. More particularly, as the gantry is rotated during a scan, the position of pre-patient collimator cams are adjusted, or moved, for each location of the gantry as determined by the combined dynamic movement error and thermal drift error.

The above described system adjusts the position of the x-ray beam to facilitate correction of z-axis x-ray beam movement of the imaging system. In addition, the described system reduces patient dosage without reducing image quality.

DETAILED DESCRIPTION OF THE INVENTION

Figure 1:
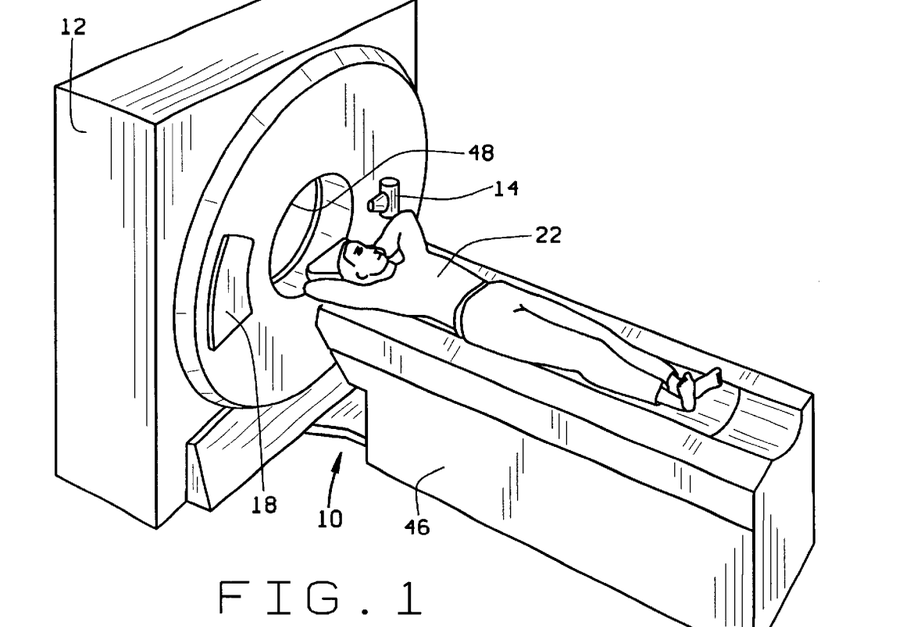
FIG. 1 is a pictorial view of a CT imaging system.
Figure 2:
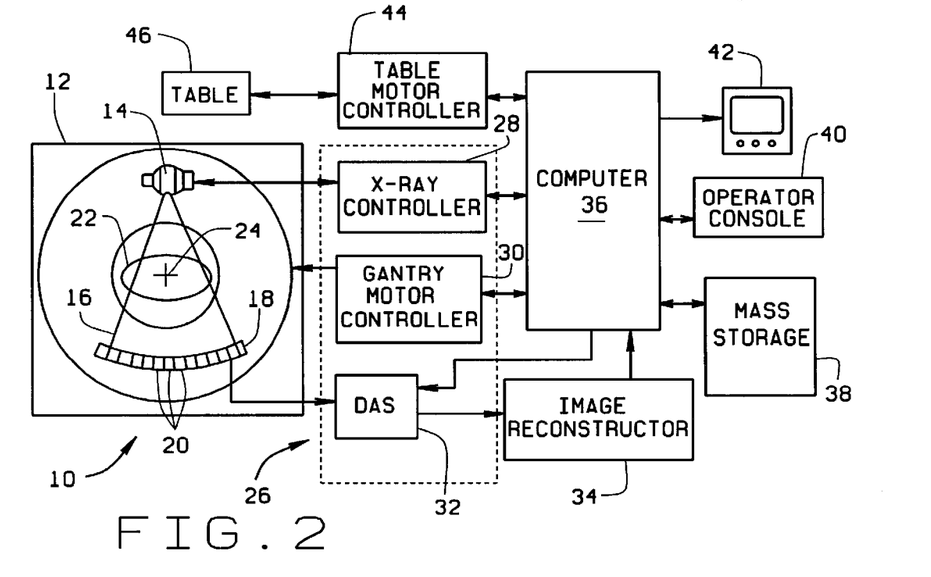
FIG. 2 is a block schematic diagram of the system illustrated in FIG.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives and supplies signals via a user interface, or graphical user interface (GUI). Specifically, computer receives commands and scanning parameters from an operator via console 40 that has a keyboard and a mouse (not shown). An associated cathode ray tube display 42 allows the operator to observe the reconstructed image and other data from computer 36. The operator supplied commands and parameters are used by computer 36 to provide control signals and information to x-ray controller 28, gantry motor controller 30, DAS 32, and table motor controller 44.

Figures 3, 4:
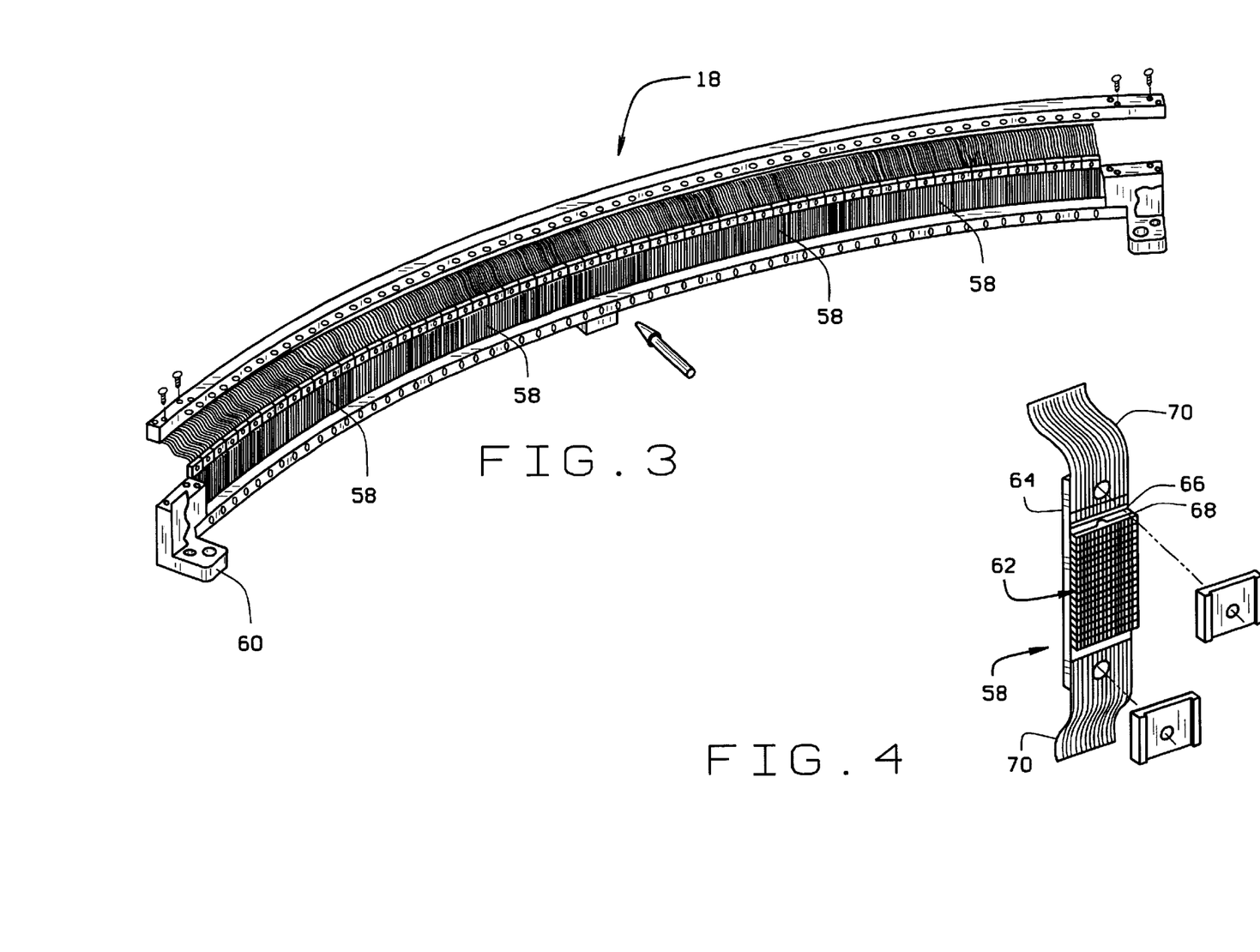
FIG. 3 is a perspective view of a CT system detector array.
FIG. 4 is a perspective view of a detector module.

As shown in FIGS. 3 and 4, detector array 18 includes a plurality of detector modules 58. Each detector module 58 is secured to a detector housing 60. Each module 58 includes a multidimensional scintillator array 62 and a high density semiconductor array (not visible). A post patient collimator (not shown) is positioned over and adjacent scintillator array 62 to collimate scattered x-ray beams before such beams impinge upon scintillator array 62. Scintillator array 62 includes a plurality of scintillation elements arranged in an array, and the semiconductor array includes a plurality of photodiodes (not visible) arranged in an identical array. The photodiodes are deposited, or formed on a substrate 64, and scintillator array 62 is positioned over and secured to substrate 64.

Detector module 58 also includes a switch apparatus 66 electrically coupled to a decoder 68. Switch apparatus 66 is a multidimensional semiconductor switch array of similar size as the photodiode array. In one embodiment, switch apparatus 66 includes an array of field effect transistors (not shown) with each field effect transistor (FET) having an input, an output, and a control line (not shown). Switch apparatus 66 is coupled between the photodiode array and DAS 32. Particularly, each switch apparatus FET input is electrically connected to a photodiode array output and each switch apparatus FET output is electrically connected to DAS 32, for example, using flexible electrical cable 70.

Decoder 68 controls the operation of switch apparatus 66 to enable, disable, or combine the outputs of the photodiode array in accordance with a desired number of slices and slice resolutions for each slice. Decoder 68, in one embodiment, is a decoder chip or a FET controller as known in the art. Decoder 68 includes a plurality of output and control lines coupled to switch apparatus 66 and computer 36. Particularly, the decoder outputs are electrically connected to the switch apparatus control lines to enable switch apparatus 66 to transmit the proper data from the switch apparatus inputs to the switch apparatus outputs. The decoder control lines are electrically connected to the switch apparatus control lines and determine which of the decoder outputs will be enabled. Utilizing decoder 68, specific FETs within switch apparatus 66 are enabled, disable, or combined so that specific outputs of the photodiode array are electrically connected to CT system DAS 32. In one embodiment defined as a 16 slice mode, decoder 68 enables switch apparatus 66 so that all rows of the photodiode array are electrically connected to DAS 32, resulting in 16 separate, simultaneous slices of data being sent to DAS 32. Of course, many other slice combinations are possible.

In one specific embodiment, detector 18 includes fifty-seven detector modules 58. The semiconductor array and scintillator array 62 each have an array size of 16×16. As a result, detector 18 has 16 rows and 912 columns (16×57 modules), which enables 16 simultaneous slices of data to be collected with each rotation of gantry 12. Of course, the present invention is not limited to any specific array size, and it is contemplated that the array can be larger or smaller depending upon the specific operator needs. Also, detector 18 may be operated in many different slice thickness and number modes, e.g., one, two, and four slice modes. For example, the FETs can be configured in the four slice mode, so that data is collected for four slices from one or more rows of the photodiode array. Depending upon the specific configuration of the FETs as defined by decoder control lines, various combinations of outputs of the photodiode array can be enabled, disabled, or combined so that the slice thickness may, for example, be 1.25 mm, 2.5 mm, 3.75 mm, or 5 mm. Additional examples include a single slice mode including one slice with slices ranging from 1.25 mm thick to 20 mm thick, and a two slice mode including two slices with slices ranging from 1.25 mm thick to 10 mm thick. Additional modes beyond those described are possible.

Figure 5:
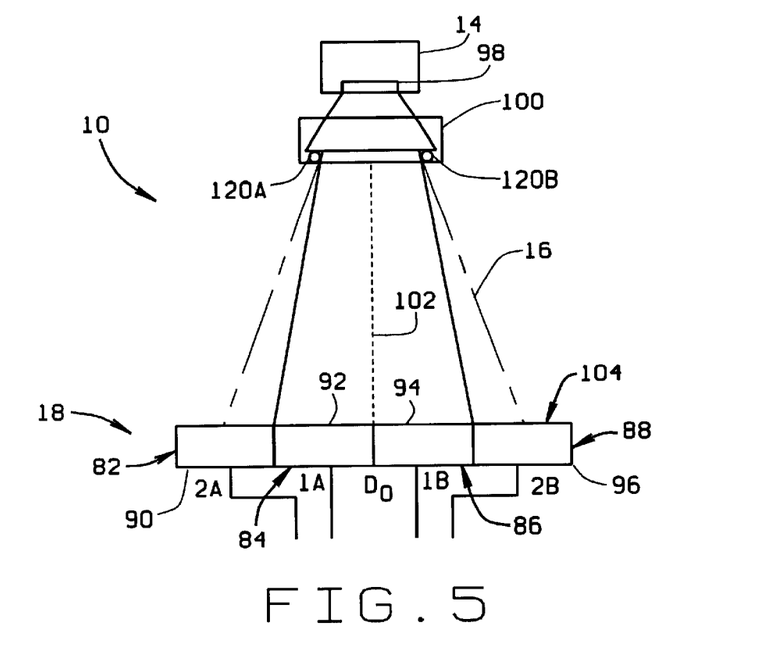
FIG. 5 is a schematic view of the CT imaging system shown in FIG. 1.

In one embodiment as shown in FIG. 5, system 10 is a "four (or quad) slice" system in that four rows 82, 84, 86 and 88 of detector cells are utilized to obtain projection data. In addition to collecting projection data, detector cells, sometimes referred to as z position cells, 90, 92, 94 and 96 are utilized for determining position of x-ray beam 16. More specifically, x-ray beam 16 emanates from a focal spot 98 of x-ray source 14 (FIG. 2). X-ray beam 16 is collimated by a pre-patient collimator 100, and collimated beam 16 is projected toward detector cells 90, 92, 94, and 96. A plane 102, generally referred to as the "fan beam plane", contains the centerline of focal spot 98 and the centerline of beam 16. In FIG. 5, fan beam plane 102 is aligned with the centerline $D_o$ of exposure area 96 on detector cells 90, 92, 94, and 96. In alternative embodiments system 10 is a multiple slice system having any number of slices; i.e. 2 slices, 3 slices, 5, or 6 slices.

In one embodiment, collimator 100 of system 10 includes eccentric cams 120A and 120B. The position of cams 120A and 120B are controlled by x-ray controller 28. Cams 120A and 120B are positioned on opposing sides of fan beam plane 102 and may be independently adjusted with respect to the spacing between cams 120A and 120B and their location relative to fan beam plane 102. Cams 120A and 120B may be positioned with a single cam drive, or alternatively, each cam may be positioned with a separate cam drive, for example a motor. Cams 120A and 120B are fabricated from an x-ray absorbing material, for example, tungsten. As a result of the eccentric shape, the rotation of respective cams 120A and 120B alters the z-axis position of x-ray beam 16. More specifically, altering position of cams 120A and 120B alters the position and width of x-ray beam umbra. Particularly, as a result of the jointly stepping eccentric shape of cams 120A and 120B, the position of x-ray beam 16 relative to detector array 18 may be altered, or adjusted. In addition, altering the position, or stepping, cam 120A, alone, alters the umbra width and position relative to one edge of detector array 18. Altering the position of cam 120B, alone, alters the umbra width and position relative to the other, or second edge, of detector array 18.

Figure 6:
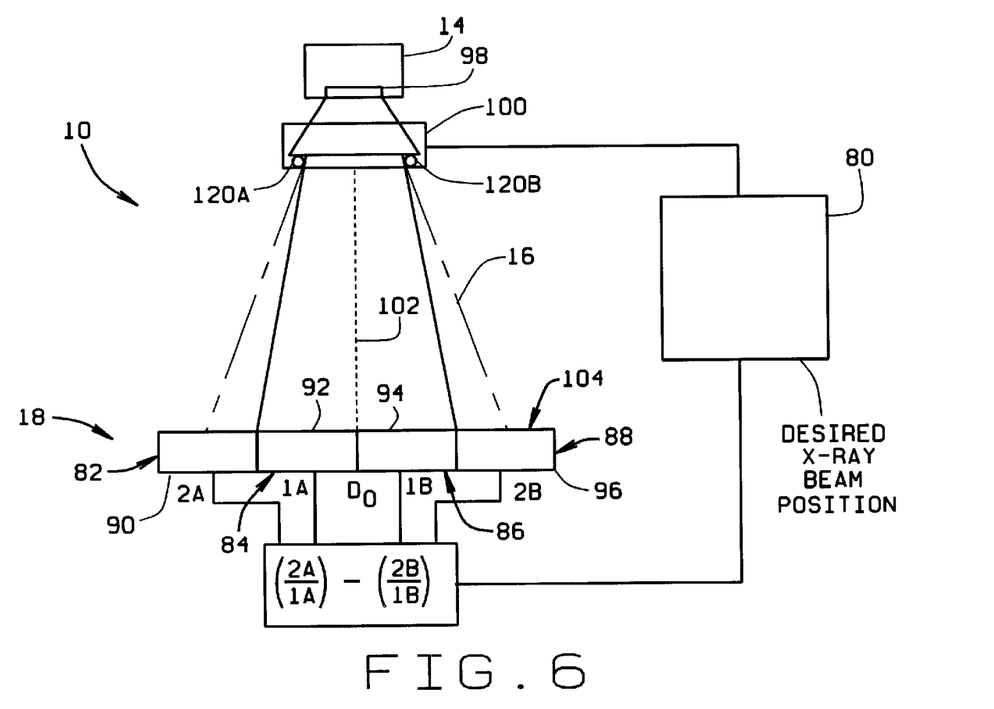
FIG. 6 is a schematic view of an the CT imaging system including a tracking control system in accordance with one embodiment of the present invention.

In one embodiment and referring to FIG. 6, system 10 includes an x-ray beam tracking control circuit, or system, 80 in accordance with the present invention. System 80, in one embodiment, is coupled to control mechanism 26 and computer 36 and utilizes a x-ray beam position error profile to correct for position errors, or movements, of x-ray beam 16 of system 10. More specifically and in one embodiment, system 80 utilizes a dynamic movement error and a thermal drift error from a first scan to correct, or compensate for, the respective dynamic movement and thermal drift errors of system 10 in a subsequent scan. Particularly, system 80 adjusts, or alters, the position of x-ray beam 16 in a subsequent rotation to correct for the position error profile from a first rotation of gantry 12 by altering the position of pre-patient collimator 100. System 80 maintains a narrow x-ray beam 16 over detector array 18 to reduce x-ray dosage to a patient without impacting, or effecting, the collection of projection data.

Specifically, the dynamic movement error is used to adjust, or correct, for the position errors of x-ray beam 16 caused by the rotation of gantry 12. More specifically, as the components of gantry 12 are rotated, including x-ray source 14 and detector array 18, gravitational and centrifugal forces cause a z-axis position error of x-ray beam 16. In one embodiment, as a result of the physics of source 14 and the design of gantry 12, the amount of z-axis x-ray beam position error, or movement, caused by the rotation of gantry 12 is fairly consistent and constant from rotation to rotation. As a result, the dynamic movement error determined by measuring the amount of x-ray beam position error caused during an initial, or first, rotation of gantry 12 may be used for subsequent rotations.

Particularly, the dynamic movement error is determined by measuring a position error of x-ray beam 16 for at least a first location, or angle, of gantry 12. In one embodiment, the position error of x-ray beam 16 is determined, or measured, for a plurality of locations, or angles, of gantry 12 utilizing the output signals from detector array 18. Particularly, for each selected location, or angle, of gantry 12, a corresponding position error is generated by determining a difference between a desired, or expected, position of x-ray beam 16 and a measured position of x-ray beam 16. In one embodiment, the measured, or actual, position of x-ray beam 16 is determined by relating the intensities of signal intensities 2A, 1A, 2B and 1B output by respective detector cells 90, 92, 94, and 96 according to the ratio $[(2A/1A)-(2B/1B)]$. In one embodiment, the ratio is determined by computer 36 and assuming a uniform x-ray beam 16 and response of detector array 18, umbra of x-ray beam 16 is centered over detector array 18 when the quantity (2A/1A) is equal to the quantity (2B/1B).

The dynamic movement error, in one embodiment, is determined by storing the x-ray beam z axis position error for each selected location of gantry 12 in a memory, for example in computer 36. The position errors are then characterized to determine the dynamic movement error for a specific speed and tilt angle of gantry 12. Particularly and in one embodiment, the measured position errors are characterized by determining a mean of the measured position errors. As a result of the rotation to rotation consistency of the position error, the dynamic movement error is then utilized for subsequent scans. Specifically, after determining the speed and tilt angle of gantry 12, the determined dynamic movement error is utilized to alter the position of collimator 100 to correct for the dynamic movement position error of x-ray beam 16. More specifically, the position of at least one of cams 120A and 120B is altered, or adjusted to alter the position of x-ray beam 16. For example, during a first scan rotation of gantry 12, the output signals A, 1A, 1B, and 2B from respective cells 90, 92, 94, and 96 are measured, or collected, using DAS 32, for each 30 degrees of rotation of gantry 12. Using the relationship $[(2A/1A)-(2B/1B)]$, the position of x-ray beam 16 is measured, or determined, and compared to the desired position of x-ray beam 16 to determine the z-axis dynamic movement position error. More specifically, the difference is determined between the measured quantity $[(2A/1A)-(2B/1B)]$ and the desired position of x-ray beam 16 for each of the twelve (360 degrees/30 degrees) locations of gantry 12. The differences are then stored and characterized for the specific gantry speed and angle to determine the dynamic movement and error.

Once the dynamic movement error is determined, the position of x-ray beam 16 may be altered to correct for dynamic movement errors. Specifically, for each selected location of gantry 12, the position of cams 120A and 120B are altered to adjust the position of x-ray beam 16 to correct for the dynamic movement error. Particularly, the position of cams 120A and 120B follow, or move, according to the dynamic movement error for each selected location. For example, in one embodiment where the characterized dynamic movement error represents a linear approximation of the dynamic movement position errors, the position of cams 120A and 120B are moved, or repositioned, every 100 ms as gantry 12 is rotated to correct for the dynamic movement position errors of x-ray beam 16.

In an alternative embodiment, the output signals 2A, 1A, 1B, and 2B are utilized to determine a z-axis dynamic movement position error for a first portion and a second portion of x-ray beam 16 with respect to x-ray beam centerline 102. More specifically, using the relationship of (2A/1A), the position of a first portion of x-ray beam 16 with respect to detector 18, i.e., width of x-ray beam 16 from centerline 102 with respect to cells 90 and 92, is determined. Similarly, the relationship (2B/1B) is used to determine the position of a second portion of x-ray beam 16 with respect to detector 18, i.e., width of x-ray beam 16 from centerline with respect to cells 94 and 96. A difference is then determined for each portion of x-ray beam 16 between the measured quantity (2A/1A) and the desired position of the first portion of x-ray beam 16. Similarly, a difference is determined between the measured quantity (2B/1B) and the desired position of the second portion of x-ray beam 16. The first portion and second portion differences are stored and characterized for the specific gantry speed and angle to determine the dynamic movement and error as described above. The position of each portion of x-ray beam 16 may then be altered to correct for dynamic movement errors.

Specifically, for each selected location of gantry 12, the position of cam 120A is altered to correct for the first portion dynamic movement error of x-ray beam 16. Similarly, for each selected location of gantry 12, the position of cam 120B is altered to correct for the second portion dynamic movement error of x-ray beam 16. Particularly, the position of cam 120A independently follows, or moves, according to the first portion dynamic movement error for each selected location. Similarly, the position of cam 120B independently follows, or moves, according to the second portion dynamic movement error for each selected location.

In one embodiment, after determining the dynamic movement error, the thermal drift error of system 10 is determined. Utilizing the thermal drift error, system 80 adjusts, or corrects, for the position error of x-ray beam 16 caused by thermal drift of system 10. In one embodiment, the thermal drift error includes an actual thermal drift and a predicted thermal drift. The actual thermal drift includes the measured amount of movement, or error of x-ray beam 16, caused by the change in temperature of system 10 during a previous rotation of gantry 12. The predicted thermal drift includes a portion of the total amount of x-ray beam thermal drift resulting from the entire temperature range of system 10 depending upon the amount of time that has passed, or elapsed, from the previous scan. In one embodiment, the z-axis position of x-ray beam 16 is altered to correct for the predicted thermal drift and the actual thermal drift caused by source 14. Particularly, the position of at least one of collimator cams 120A and 120B is moved so that the position of x-ray beam 16 is corrected for the thermal drift error. For example, the actual thermal drift error may be 0.002 mm maximum during a previous one second rotation of gantry 12 and the predicted thermal drift error of system 10 may be 0.6 mm when the previous scan was completed sixty minutes ago.

More specifically, prior to completing a first, or initial, scan, a predicted thermal drift profile is determined. The predicted thermal drift profile is determined by measuring the thermal drift of the system 10 as a function of time. The predicted thermal drift profile of system 10 is determined by measuring, or determining, the amount of thermal drift of system 10 for at least one point in time using detector 18. Particularly and in one embodiment, the predicted thermal drift profile of system 10 is determined for a plurality of points in time as the temperature of source 14 is varied from an ambient temperature to a maximum operating temperature and allowed to cool again to the ambient temperature. For each point in time, the amount of thermal drift error is measured, or determined, utilizing detector 18. More specifically and as described above, a difference between the 2A, 1A, 1B, 2B, output signal from respective cells 90, 92, 94, and 96 and the desired position is utilized to determine the z-axis position of x-ray beam 16 as a result of thermal drift.

Figure 7:
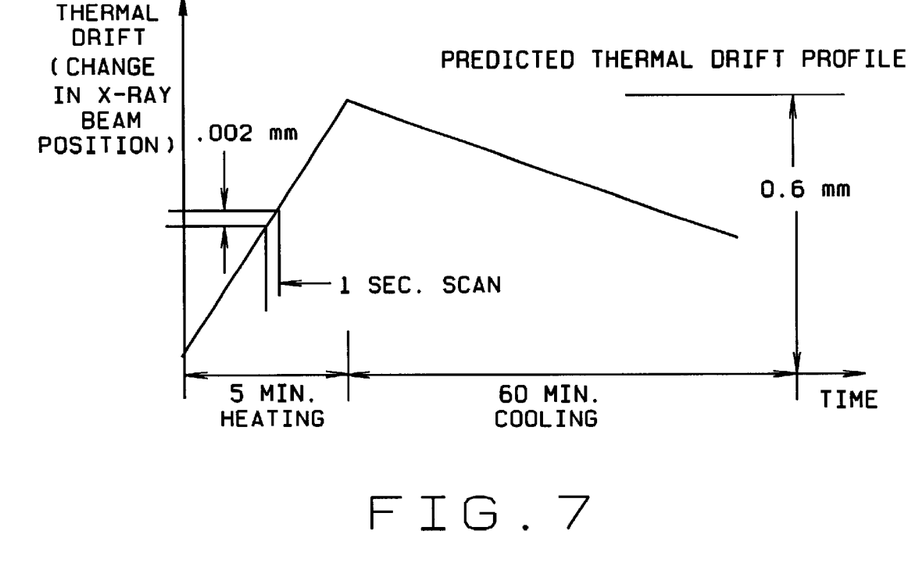
FIG. 7 is a graph illustrating a predicted thermal drift profile in accordance with one embodiment of the present invention.

Referring to FIG. 7 and in one embodiment, the predicted thermal drift profile is determined by applying a linear function to the measured, or determined thermal drift error for each point in time over the temperature range of system 10. In an alternative embodiment, the predicted thermal drift profile is determined by applying an exponential decay function to the determined thermal drift error of x-ray beam 16. Utilizing the predicted thermal drift profile and the period of time from a previous scan, the predicted thermal drift of system 10 is determined.

After determining the predicted thermal drift, a first, or initial, scan is completed, or performed. Prior to performing the scan, the position of x-ray beam 16 is adjusted, i.e., using collimator 100, to correct for the predicted thermal drift. As the scan is being completed, at least one actual thermal drift position of x-ray beam 16 is determined using detector 18. Specifically, a plurality of actual thermal drift positions are determined, or measured, using detector 18 as gantry 12 completes a first rotation, or segment. In one embodiment, the actual thermal drift is then determined for the first rotation by determining an average of the measured actual thermal drift positions. The actual thermal drift is then utilized for a subsequent rotation to adjust, or correct, for the actual thermal drift from the previous rotation of gantry 12.

In operation, just prior to starting a second, or subsequent, scan of patient 22, collimator 100 is pre-positioned, or moved, based on the thermal drift error of system 10. More specifically, the actual thermal drift and predicted thermal drift are combined to correct for the thermal drift of system 10. Particularly, for the scan, a time period from the completion of the prior rotation or segment, using a timer (not shown), is determined. Utilizing the predicted thermal drift profile and the time period from the previous rotation, the predicted thermal drift is determined. In one embodiment, the actual thermal drift is then combined with the predicted thermal drift to determine the position of collimator 100. More specifically, the position of cams 120A and 120B are pre-positioned, or moved, to correct for the combined predicted thermal drift and the actual thermal drift from the previous rotation.

In one embodiment, as a result of x-ray source 14 typically being energized prior to beginning a scan, the actual thermal drift of x-ray beam 16 is measured, or determined, using a shortened update interval, so that collimator 100 is properly positioned before gantry 12 begins to rotate. Specifically, the actual thermal drift is determined as described above by determining a difference between the measured position and desired position of x-ray beam 16 just prior to the rotation of gantry 12. The position of cams 120A and 120B are adjusted to correct for any difference between the desired position and the measured position.

Figure 8:
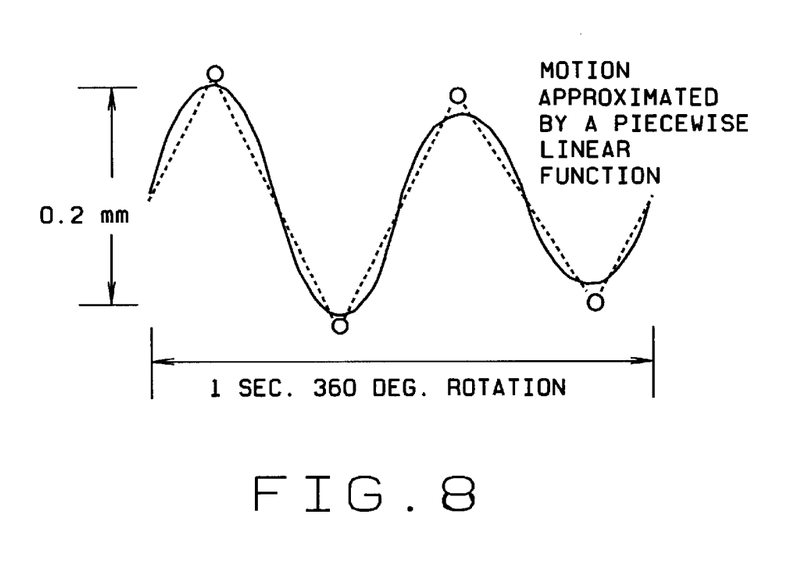
FIG. 8 is a graph illustrating movement of collimator cams versus time.

As gantry 12 begins to rotate, the position error profile adjusts the z-axis position of x-ray beam 16 to correct for the dynamic movement and thermal drift error of system 10. More specifically, as gantry 12 rotates, the position of collimator 100 is adjusted to correct for dynamic movement error and the thermal drift error. Particularly, as gantry 12 is rotated, the position of collimator 100 is adjusted to adjust for the combined constant previous rotation thermal drift error and the changing dynamic movement error for each desired location. The position of cams 120A and 120B follow, or move, according to the combined position error profile, for example, a linear approximation of the quantity of the constant thermal drift error plus the dynamic movement error. For example and in one embodiment shown in FIG. 8, the position of cams 120A and 120B are moved, or repositioned 50 times during a one second rotation of gantry 12. Specifically, the position of cams 120A and 120B are moved to reflect the synchronized combination of the dynamic movement error for the selected speed and tilt angle of gantry 12 and the thermal drift error. As a result, the position of x-ray beam 16 is adjusted to correct for the dynamic movement error and the thermal drift error so that patient dosage is reduced without reducing image quality.

In yet another embodiment, the dynamic movement error and the thermal drift error are updated on a selected time or event driven basis. For example, the respective errors may be replaced, or updated, every selected number of hours, i.e., every 100 operating hours, or number of days, i.e., every 30 calendar days. Similarly, the dynamic movement error and thermal drift error may be replaced or updated each time a component within gantry 12 is replaced or repaired, for example each time source 14 or detector 18 is replaced or repaired. Additionally and in one embodiment, at least two historical, or past, dynamic movement error may be utilized to determine a difference history dynamic movement error. The difference history dynamic error may then be used to determine the dynamic movement error. Specifically, and in one embodiment, the historical errors are averaged together to determine the dynamic movement error. In an alternative embodiment, a recursive filter is applied to the historical errors to determine the dynamic movement error.

In another embodiment, at lease one actual position error is generated or determined, during each rotation, or scan. The actual position error monitors system 10 to detect excessive errors. If the actual position error exceeds a preselected limit or range, a corrective action is performed, or completed. For example, if the actual error exceeds the preselected limit, the corrective action includes aborting or terminating, the present scan. In another embodiment, the corrective action includes logging a service request. In yet another embodiment, where the actual errors are generated by blockages of detector array 18, system 80 requires a defined, or selected, number of excess actual errors prior to generating the corrective action.

The above described correction system adjusts the position of x-ray beam to correct for dynamic and temperature movements of the imaging system. In addition, the x-ray beam position is optimized to reduce patient dosage without reducing image quality.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Similarly, while the systems described herein has been four-slice, any multi-slice system may be used, e.g. two-slice, three-slice, and six-slice. Moreover, while the tracking correction system has been described in detail, the position of the x-ray beam may be adjusted by altering the position of x-ray source 14 and/or detector array 18. Accordingly, the spirit and scope of the invention are to be limited only by the terms of the appended claims.

What is claimed is:

1. A method for correcting x-ray beam drift in a computed tomography (CT) imaging system having a rotating gantry, a multislice detector array having at least two rows of detector cells, and an x-ray source configured to radiate an x-ray beam toward the detector array, wherein the multislice detector array and the x-ray source are coupled to the rotating gantry; said method comprising the steps of:

initially collimating the x-ray source to correct for a predicted thermal drift of the x-ray beam prior to an initial scan;

scanning the object during an initial scan using the initially collimated x-ray source and adjusting the collimation during the initial scan using a predicted dynamic movement error profile of the x-ray beam;

measuring a position error of the x-ray beam during the initial scan to determine a mean position error during the initial scan; and adjusting the collimation in a subsequent scan to correct for the determined mean position error.

2. A method in accordance with claim 1 and further comprising the step of determining the x-ray beam dynamic movement error for a first rotation of the gantry.

3. A method in accordance with claim 2 wherein determining the x-ray beam dynamic movement error comprises the steps of:

determining a measured x-ray beam position for at least a first location of the gantry using the detector array;

determining a desired x-ray beam position for each measured x-ray beam position; and determining a difference between each measured x-ray beam position and each desired x-ray beam position.

4. A method in accordance with claim 3 wherein determining the measured x-ray beam position utilizing the detector array comprises the steps of:

obtaining separate signals from at least a first detector cell in a first detector cell row, at least a second detector cell in a second detector cell row, at least a third detector cell in a third detector cell row, at least a fourth detector cell in a fourth detector cell row of the detector array; and determining the x-ray beam position from the intensities of the separate signals.

5. A method in accordance with claim 4 wherein the signal from the first detector cell has an intensity 2A, the signal from the second detector cell has an intensity of 1A, the signal from the third detector cell has an intensity of 1B, and the signal from the fourth detector cell has an intensity of 2B, and wherein determining the x-ray beam position from the intensities of the separate signals is determined using the relationships of (2A/1A) and (2B/1B).

6. A method in accordance with claim 3 wherein determining a measured x-ray beam position for at least a first location comprises the step of determining a measured x-ray beam position for a plurality of gantry locations.

7. A method in accordance with claim 3 wherein the system further includes a memory, and said method further comprising the step of storing each difference in the memory.

8. A method in accordance with claim 3 further comprising the step of generating a difference history profile.

9. A method in accordance with claim 8 wherein generating the difference history profile comprises the step of generating an average of at least two dynamic movement error profiles.

10. A method in accordance with claim 8 wherein generating the difference history profile comprises the step of applying a recursive filter to at least two dynamic movement error profiles.

11. A method in accordance with claim 2 further comprising the step of determining an x-ray beam thermal drift error.

12. A method in accordance with claim 11 wherein determining an x-ray beam thermal drift error comprises the steps of:

determining an actual thermal drift; and determining a predicted thermal drift.

13. A method in accordance with claim 12 wherein determining the predicted thermal drift comprises the steps of:

determining a predicted thermal drift profile; and determining a period of time from a previous rotation of the gantry.

14. A method in accordance with claim 1 wherein the system further includes a pre-patient collimator having a plurality of positions for altering the z-axis position of the x-ray beam, wherein adjusting the x-ray beam position for the subsequent scan based on the determined x-ray beam position error profile comprises the step of altering the position of the pre-patient collimator.

15. A method in accordance with claim 14 wherein the pre-patient collimator includes at least a first cam and a second cam positioned on opposing sides of the x-ray beam, and wherein altering the position of the pre-patient collimator comprises the step of alter a position of at least one of the first cam and the second cam.

16. A method in accordance with claim 1 further comprising the steps of:

determining at least one actual position error during the first scan;

determining if the difference exceeds a pre-selected limit; and if the determined difference exceeds the pre-selected limit then performing a corrective action.

17. A method in accordance with claim 16 wherein performing the corrective action comprises the step of aborting a scan.

18. A method in accordance with claim 16 wherein performing the corrective action comprises the step of logging a service request.

19. A beam tracking control system for correcting x-ray beam drift in a computed tomography (CT) imaging system having a rotating gantry, a multislice detector array having at least two rows of detector cells, and an x-ray source configured to radiate an x-ray beam toward the detector array, wherein the multislice detector array and x-ray source are configured to rotate with the rotating gantry to scan an object; said control system configured to:

initially collimate an x-ray source of a CT imaging system to correct for a predicted thermal drift of the x-ray beam prior to an initial scan;

adjust the collimation during the initial scan using a predicted dynamic movement error profile of the x-ray beam;

measure a position error of the x-ray beam during the initial scan to determine a mean position error during the initial scan; and adjust the collimation in a subsequent scan to correct for the determined mean position error.

20. A control system in accordance with claim 19 further configured to determine an initial x-ray beam dynamic movement error.

21. A control system in accordance with claim 20 wherein to determine the initial x-ray beam dynamic movement error, said control system is configured to:

determine a measured x-ray beam position;

determine a desired x-ray beam position for each measured x-ray beam position; and determine a difference between each measured x-ray beam position and each desired x-ray beam position.

22. A control system in accordance with claim 21 wherein to determine the measured x-ray beam position, said control system is configured to:

obtain separate signals from at least a first detector cell in a first detector cell row, at least a second detector cell in a second detector cell row, at least a third detector cell in a third detector cell row, at least a fourth detector cell in a fourth detector cell row of a detector array of the CT imaging system; and determine the x-ray beam position from intensities of the separate signals.

23. A control system in accordance with claim 22 wherein the separate signals have intensities of 2A, 1A, 1B, and 2B, and said beam tracking control system is configured to determine the x-ray beam position using relationships (2A/1A) and (2B/1B).

24. A control system in accordance with claim 21 wherein to determine a measured x-ray beam position, said control system is configured to determine measured x-ray beam positions corresponding to a plurality of locations of a gantry of the CT imaging system.

25. A control system in accordance with claim 21 wherein said control system is further configured to store each difference in a memory of the CT imaging system.

26. A control system in accordance with claim 21 further configured to generate a difference history profile.

27. A control system in accordance with claim 25 wherein to generate the difference history profile, said control system configured to generate an average of at least two dynamic movement error profiles.

28. A control system in accordance with claim 26 wherein to generate the difference history profile, said control system is configured to apply a recursive filter to at least two dynamic movement error profiles.

29. A control system in accordance with claim 21 further configured to determine an x-ray beam thermal drift error.

30. A control system in accordance with claim 29 wherein to determine the x-ray beam thermal drift error, said control system is configured to:

determine an actual thermal drift; and determine a predicted thermal drift.

31. A control system in accordance with claim 30 wherein to determine the predicted thermal drift, said control system configured to:

determine a predicted thermal drift profile; and determine a period of time from a rotation of a gantry of the CT imaging system.

32. A control system in accordance with claim 19 wherein to adjust the x-ray beam position, said control system is configured to alter a position of a pre-patient collimator of the CT imaging system.

33. A control system in accordance with claim 32 wherein to alter the position of the pre-patient collimator, said control system configured to alter a position of at least one of a first cam and a second cam of the pre-patient collimator.

34. A control system in accordance with claim 19 further configured to:

determine at least one actual position error during a first scan of the CT imaging system;

determine if the position error exceeds a pre-selected limit; and when the determined position error exceeds the pre-selected limit, perform a corrective action.

35. A control system in accordance with claim 34 wherein to perform the corrective action, said control system is configured to abort a scan of the CT imaging system.

36. A control system in accordance with claim 34 wherein to perform the corrective action, said control system configured to log a service request.

* * * * *